United States Patent [19]

Cryer et al.

[11] Patent Number: 5,631,009
[45] Date of Patent: May 20, 1997

[54] PORCINE ADIPOCYTE ANTIGENS AND THEIR USE IN THE IMMUNOLOGICAL CONTROL OF FAT

[75] Inventors: Anthony Cryer, South Glamorgan, Wales; David J. Flint, Alloway, Scotland; Steven C. Kestin, Langford, England

[73] Assignee: British Technology Group Ltd., England

[21] Appl. No.: 211,033

[22] PCT Filed: Sep. 18, 1992

[86] PCT No.: PCT/GB92/01721

§ 371 Date: Mar. 17, 1994

§ 102(e) Date: Mar. 17, 1994

[87] PCT Pub. No.: WO93/06131

PCT Pub. Date: Apr. 1, 1993

[30] Foreign Application Priority Data

Sep. 19, 1991 [GB] United Kingdom ............. 9120037

[51] Int. Cl.$^6$ ............... A61K 39/00; A61K 38/00; A61K 35/12; C07K 16/00

[52] U.S. Cl. ............. 424/184.1; 424/520; 424/574; 514/21; 530/350; 530/387.1; 530/388.1; 530/389.1; 530/403

[58] Field of Search ............. 424/184.1, 520, 424/574; 530/350, 388.1, 387.1, 389.1, 403; 514/21

[56] References Cited

U.S. PATENT DOCUMENTS

| | | | |
|---|---|---|---|
| 5,096,706 | 3/1992 | Flint | 424/88 |
| 5,102,658 | 4/1992 | Flint | 424/85.8 |

OTHER PUBLICATIONS

J. Killefer et al, J. Cell. Biochem., vol.44, No. 3 (1990) 167–175.

A. Nassar et al, Comp. Biochem. Physiol., vol. 98B, No. 213, (1991), 361–367.

Tam. et al. 1989. J. Immunological 124:53–61.

*Primary Examiner*—James C. Housel
*Assistant Examiner*—N. M. Minnifield
*Attorney, Agent, or Firm*—Graham & James LLP

[57] ABSTRACT

Antigens present in the plasma membrane of mature porcine white adipocytes, which are not present in porcine liver, kidney, spleen, brain, cardiac muscle, skeletal muscle or lung or in porcine erythrocytes, which react with antisera raised against said adipocytes and which on SDS-PAGE give rise to protein bands of relative molecular mass (r.m.m.) about 37, 50, 51 and 121 KiloDaltons, respectively and antibodies thereto are useful for the reduction of fat in pigs.

6 Claims, 6 Drawing Sheets

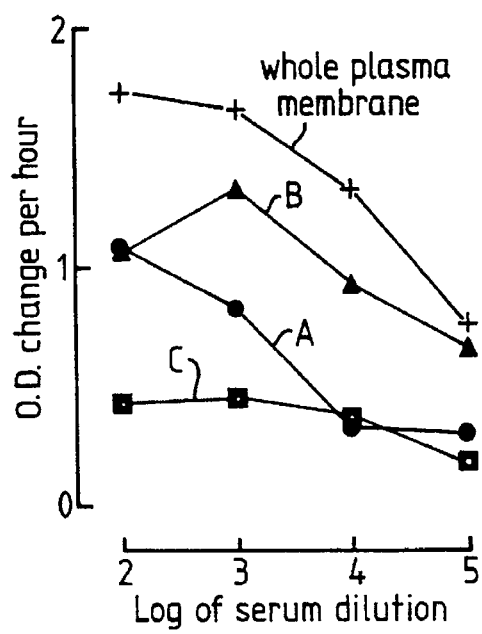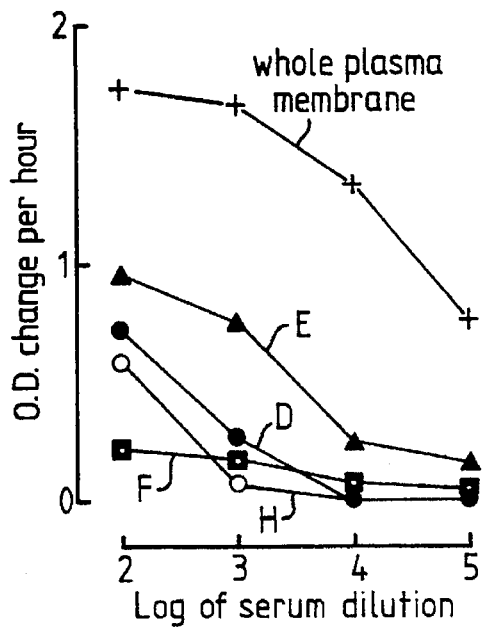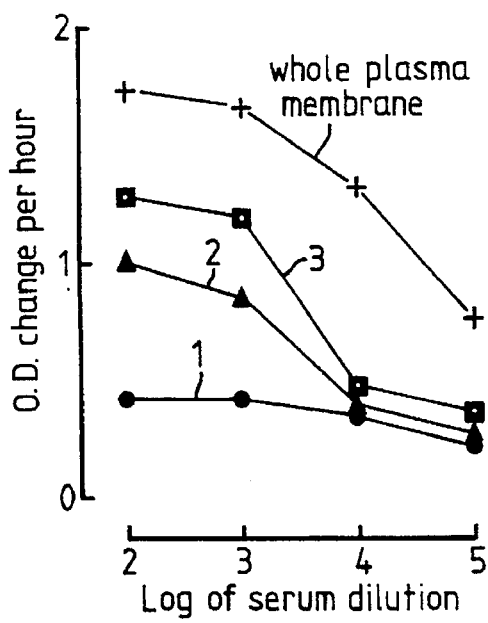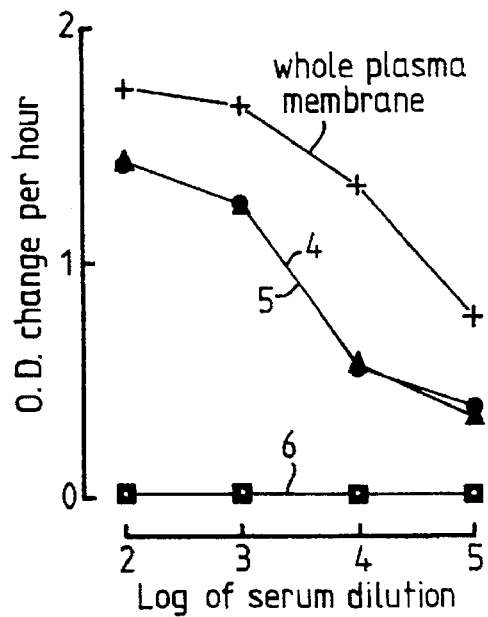

PORCINE ADIPOCYTE ANTIGENS AND THEIR USE IN THE IMMUNOLOGICAL CONTROL OF FAT

BACKGROUND OF THE INVENTION

1. Field of the Invention

This invention relates to the immunological control of fat in the mammalian body, especially in non-human animals (herein referred to simply as animals).

2. Description of Prior Art

Excess fat in animals is recognised as detrimental to lowering production costs and a health risk to human consumers. One attempt at reducing the deposition of fat in animals has been to incorporate a β-agonist in the feed. β-agonists have encountered many problems, particularly that they can adversely affect meat quality and its preservation during storage and that the animals have to be slaughtered within a short period after the compound is withdrawn from the feed. Another attempt has been the use of growth hormones such as bovine somatotrophin (BST). Besides stimulating milk yield, BST improves the protein:fat ratio and feed conversion efficiency in cattle. Although the dairy industry considers BST to be safe, it has been the subject of considerable concern to regulatory authorities and consumer groups.

In view of these problems, D J Flint et al., International Journal of Obesity 1, 69–77 (1986) pioneered the idea of raising antibodies to the plasma membranes of adipocytes and injecting them into animals. It was found that this treatment reduced the amount of fat considerably and that this reduction was maintained for several months without inducing adverse effects. The first published reports, in which crude antisera raised against whole adipocyte plasma membranes from rats were shown to have such an effect, were by D J Flint, H Coggrave, C E Futter, M J Gardner and T Clarke, International Journal of Obesity 1, 69–77 (1986) and by D J Flint and C E Futter, Annual Report of the Hannah Research Institute, Ayr, Scotland 1986. Not only was fat reduced, that there was a body weight gain and an improvement in feed conversion efficiency. In an article "Can obesity be controlled?" by D J Flint, C E Futter and M Peaker, News in Physiological Sciences 2, 1–2 (February 1987), it is reported that similar antibodies have been produced against sheep and pig fat cells and that all are effective against adipocytes in vivo. A more detailed report on the effects of treatment of Fats with anti-adipocyte antibodies is given by D Panton, C E Futter, S Kestin and D J Flint in American Journal of Physiology 258, (Endocrinol. Metab. 21): E985–E989 (1990). See also A P Moloney and P Allen, Proc. Nutrition Society, July 1988 Meeting, page 14. Although J Killefer and C Y Hu, Proc. Soc. Exp. Biol. Med. 194, 172–176 (1990) have reported raising a monoclonal antibody to pig adipocyte plasma membranes, the hybridoma is believed not to be publicly available and the paper contains no evidence that the antibody would lyse fat cells. J T Wright and G J Hausman, Int. J. Obesity 14, 395–409 (1990) report the preparation of monoclonal antibodies against porcine adipocyte plasma membranes of 2-week old pigs. The antibodies are reported to immunoprecipitate proteins of relative molecular mass 77 and 90 kD. These experiments were directed to identifying cell surface antigens useful as markers of differentiating adipocytes.

J. Killefer and C Y Hu, J. Cell. Biochem. 44, 167–175 (1990) describe a 64 kD protein present in the plasma membrane of adipocytes and genetically lean pigs, but not in adipocytes of genetically obese pigs.

Although some of the above work has demonstrated experimentally the possibility of treating fat deposition in vivo by the administration of anti-adipocyte antibodies, it is a problem that the production of such antibodies may be very labour-intensive. The administration of the plasma membranes themselves as antigens could be considered, if they could be conjugated to carrier proteins and could thereby by made "non-self". However, the production of plasma membrane material from slaughterhouses poses difficulty of quality control. If the antigen(s) responsible for the fat reduction could be isolated and purified, the way would be open to making them by a recombinant DNA method or by protein synthesis.

SUMMARY OF THE INVENTION

After considerable research, the inventors have isolated from porcine fat cell plasma membranes, antigens which appear to be specific to adipocytes (at least in the sense of not being detectable in many other body tissues of the animal) and reactive with antibodies to fat cell plasma membranes. However, not all of these antigens give rise to antisera which do, in fact, reduce fat cell deposition in vivo. After tests of sheep anti-porcine fat cells plasma membranes in vivo on pigs, the inventors have found certain antigens which can produce such antibodies. Accordingly, the present invention provides 4 antigens present in the plasma membrane of mature porcine white adipocytes, which are not present in porcine liver, kidney, spleen, brain, cardiac muscle, skeletal muscle or lung or in porcine erythrocytes, which react with antisera raised against said adipocytes and which on SDS-PAGE give rise to protein bands of relative molecular mass (r.m.m.) about 37 (A), 50 (B), 51 (C) and 121 (D) KiloDaltons, respectively, as determined by markers of relative molecular mass 29, 45, 66, 97, 116 and 205 KiloDaltons. These values for proteins A, B, C and D are expressed as the nearest whole number and are subject to possible error of up to about 2.5%.

12 candidate antigens designated 1a, 1b, 2–6, A–F and H, all potentially fat cell specific, were resolved by SDS-PAGE, with difficulty. The only way in which It could be determined whether they would reduce fat deposition was to raise antibodies and test them in pigs. As a result of these tests it was determined that A, B, C and D, at least, are active.

The invention also provides the use of such antigens and antibodies thereto for the active or passive immunisation of sheep.

BRIEF DESCRIPTION OF THE DRAWINGS

FIG. 3 shows ELISA data for reactivity to whole adipocyte plasma membranes of various antisera raised against the candidate antigens;

DESCRIPTION OF THE PREFERRED EMBODIMENTS

Figure 1:
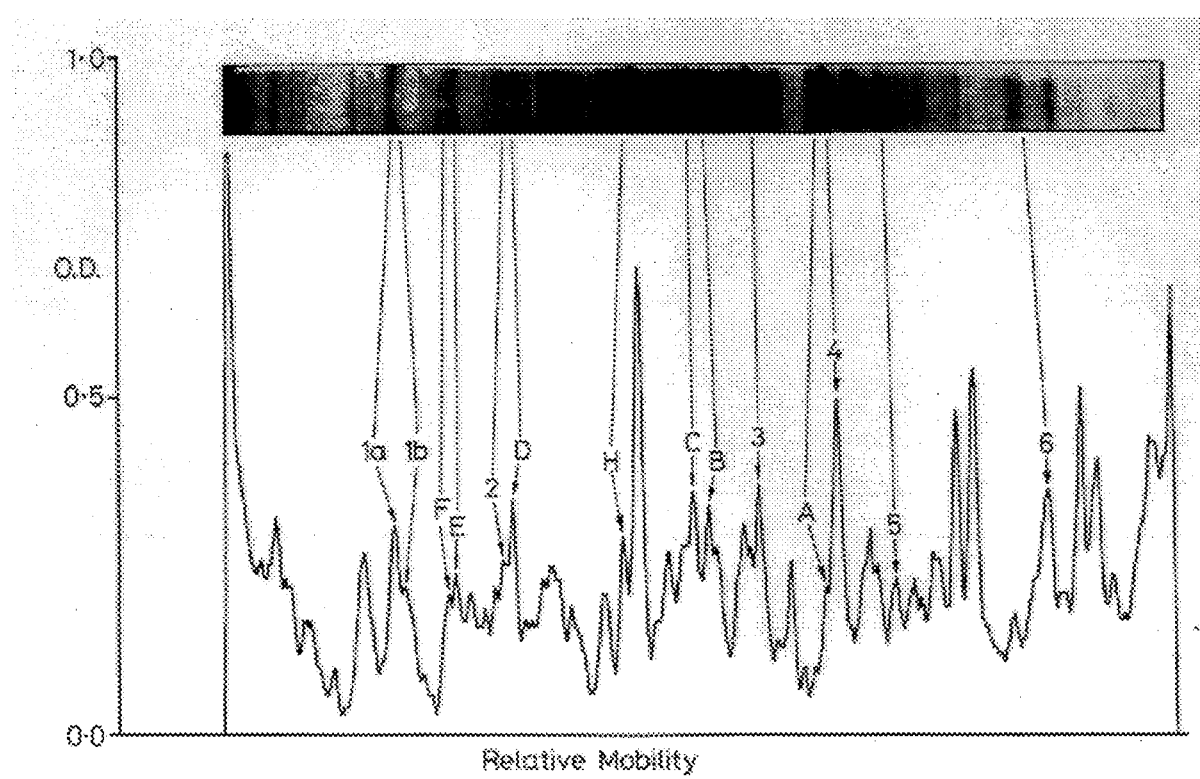
FIG. 1 shows a Coomassie blue stained gel of porcine adipocyte plasma membrane polypeptides separated by SDS-PAGE with a laser densitometry scan profile, showing the positions of the candidate antigens.

The adipocyte membranes used to prepare the antigens can be obtained from any porcine breed as it is likely that they will be highly conserved between breeds. It is suggested that they be obtained from mature white adipocytes. A mature adipocyte is one which demonstrates morphologically and biochemically the adipocyte phenotype including the presence within the cell of a large central unilocular lipid droplet. All references to "adipocytes" herein mean mature adipocytes. It is also suggested that the adipocytes be obtained by a gentle procedure which does not damage them and which removes extracellular material. It has been found that a *Clostridium histolyticum* collagenase enzyme is particularly useful for such removal. The cells are then allowed to recover by a conditioning step of incubation at a temperature of 37° C. for a period of several hours, e.g. 2 to 24 hours.

The adipocytes can then be separated and washed by flotation, retaining the floating adipocyte layer, which is then homogenised and the plasma membranes separated on a discontinuous sucrose gradient. It is then necessary either to remove non adipocyte-specific antigens or to identify which of the antigens present in the extract are adipocyte-specific. For this purpose, other porcine tissue is required. The greater the number of Kinds of tissue employed for this purpose, the better the chances will be of obtaining adipocyte-specific antigens. The inventors have found it preferable to make a direct protein band immunoblot comparison by running plasma membrane extracts prepared from various porcine tissues on SDS-PAGE, Western blotting and then immunoblotting specific protein bands with antibodies raised against plasma membranes of adipocytes. This immunodetection was carried out with difficulty, by scanning laser densitometry. Comparing the laser scans from the adipocyte plasma membranes with those from other tissues, 12 candidate "adipocyte specific antigens" were identified from the blots of a large number of proteins.

In order to generate sufficient material by this method, large scale preparations were carried out on SDS-PAGE and the bands containing each of the 12 antigens were cut from the gels and proteins were then electroeluted therefrom. Antisera were raised against the 12 electroeluted products and 10 of these were found to react immunogenically with whole adipocyte plasma membranes. The antisera were then tested in vivo by passive immunisation of pigs by local injections into areas of the body having significant subcutaneous fat. The largest lesions, indicating the reduction of fat, resulting from this treatment were those induced by anti-whole adipocyte plasma membranes, anti-antigen A and anti-antigen C, although some useful results were obtained from antigens B and D. The invention therefore includes these antigens. D is currently thought to have the weakest effect.

The information given herein enables antigens to be identified, isolated and, by methods well known in the art, purified. It is then possible to prepare antibodies by conventional raising of antisera or production of monoclonal antibodies by the Köhler-Milstein method and variations thereon. Immunogenic portions of natural antibodies are also included within the scope of the term "antibodies" as used herein, as are also hybrid human-mouse antibodies and other antibody-like products obtainable by recombinant DNA methods.

The antibodies thereby produced will be used to help identify antigens from the adipocyte membrane by a recombinant DNA method. The preparation of such antigens was begun by producing a cDNA library from RNA obtained from isolated adipocytes using a guanidinium isothiocyanate extraction method (Chomczynski and Sacchi, Analyt. Biochem. 162, 156–159 [1987]) followed by affinity chromatography to enrich for poly A+ RNA (Avid and Leder, Proc. Natl. Acad. Sci. (USA) 69, 1408–1412 [1972]). The cDNA prepared from this enriched RNA was inserted into the phage expression vector $\lambda$gt 11. The correct clones will be identified by using either the antibodies previously mentioned (Mienendorf et al., Methods in Enzymology 152, 451–457 [1987]) or by synthesising a mixture of the most probably complementary oligonucleotides, as determined from amino acid sequence of the antigens and considerations of normal DNA codon usage, as probes. The clones thus identified and isolated, after confirming their binding of antibody, can be used to express the protein of interest.

The main use of the invention will be for the treatment of excess fat production In pigs. While either active or passive immunisation is likely to have an effect, active immunisation is preferred and for this purpose the antigen will have to be made "non-self" so that it does not suffer host immune tolerance. This can be achieved by any of the conventionally explored methods, especially by conjugation to a carrier protein such as rabbit serum albumin or KLH. Epitopes of the antigen can be identified thereby enabling shorter-chain peptides to be used as immunogens. The Invention includes these within its scope. Such peptides can also be used In the form of conjugates or other elaborated structures such as branched forms thereof, in which the peptide is presented on "arms" of a carrier such as a branched lysine core.

The favoured proposed route of administration for active immunisation is by subcutaneous injection. Amounts of antigen in the range of 1 μg to 1 g per treatment are envisaged, the animal being treated preferably once only for reasons of convenience of husbandry. Adjuvants such as small components of Freund's Complete Adjuvant or peptides can be employed. Oral or nasal routes are possible alternatives.

For passive administration, the antibodies are preferably given without an adjuvant, again preferably by subcutaneous injection. Other routes such as intraperitoneal or oral are possible.

The following Examples illustrate the invention.

EXAMPLE

Section 1

Isolation of mature white adipocytes from porcine adipose tissue

Methods

Adipose tissue was collected from the following depots of freshly killed pigs: channel, mesenteric, perirenal and subcutaneous. The mixed adipose tissue was finely minced and collagenase at 1 mg/ml in medium 199 (Gibco Biocult) and 1% normal pig serum was added (20 ml of medium to 10 g tissue). The tissue was shaken at 37° C. for 1.5 hours and isolated adipocytes obtained by straining through a sieve. The adipocytes were washed three times by flotation and then conditioned for 2 hours in medium 199 containing 1% normal pig serum at 37° C. The isolated adipocytes were stored at −20° C. until used.

The cells isolated in this manner have been shown to be greater than 90% Intact and viable using standard cell viability tests, and maximal immunoreactivity had been achieved.

Section 2

The isolation and preliminary characterisation of plasma membrane preparations from conditioned porcine adipocytes Methods Adipocytes, isolated and conditioned as described in Section 1, were used for the preparation of plasma membranes. Typically, 30 ml of adipocytes were mixed with 30 ml of sucrose-based extraction medium (0.25M sucrose, 10 mM Tris-HCl, pH 7.4, 2 mM EDTA, 2 mM PMSF phenylmethyl sulphonyl fluoride) prewarmed to 37° C. The suspended cells were then disrupted by mixing for 3×30 sec on a vortex mixer. The final homogenate was centrifuged at 1000 g.av. for 5 min. Following centrifugation, the material beneath the floating plug of fat was removed by aspiration and kept on ice. This was then centrifuged at 100,000 g for 1 hour. The supernatant was then removed and the pellet resuspended in 2 ml of 50 mM Tris buffer using a plastic Pasteur pipette. Discontinuous sucrose density gradient centrifugation was then used to separate mitochondria and other components from the plasma membranes. The membranes were removed from the 0/32% sucrose interface and pelleted at 100,000 g for 1 hour at 4° C. The pellet was resuspended in 50 mM Tris HCl, pH 7.4 and stored at −20° C. until used.

Section 3

The replicated SDS-PAGE analysis of the pattern of polypeptides from porcine adipocyte plasma membranes Methods Preparation and running of analytical gels The above-prepared plasma membranes from porcine adipocytes were analysed by SDS-PAGE using a linear gradient of polyacrylamide concentration between 5 and 15% for the resolving gel. The gels were prepared and run by a modification of the procedure originally outlined by Laemmli, Nature 227, 680–685 (1970) in a vertical electrophoresis unit (Atto Corporation) according to the manufacturer's instructions. The electrophoresis was performed in 7 by 8 cm "minigels" (0.75 mm thick). See also Tume, Lee and Cryer, Comp. Biochem. Physiol. 80B, 127–134 (1985).

Protein standards (Biorad high molecular weight 205, 116, 97, 66, 45 and 29 KiloDaltons were heated to 37° C. for 2 hours in the presence of an equal volume of loading buffer. [1.0 ml stacking gel buffer, 0.125M Tris-HCl, pH 6.8, containing 0.1% (w/v) SDS, 400 µl 10% glycerol, 200 µl 2-mercaptoethanol, 100 µl 0.25% bromophenol blue, 300 µl distilled water]. Pig adipocyte plasma membranes were treated in similar fashion for 30 min. Electrophoresis was performed at 150 V constant voltage. The electrode buffer used was 0.25M Tris containing 0.192M glycine and 0.1% (w/v) SDS, at pH 8.3.

Staining and destaining of gels

Gels were immersed for 1–2 hours in 0.125% (w/v) Coomassie Brilliant Blue in 10% (v/v) glacial acetic acid containing 40% methanol. To visualise protein bands, the gels were then destained in repeated changes of 10% (v/v) acetic acid in 30% (v/v) methanol.

Calibration using Standards of Known relative molecular mass

The relationship between relative molecular mass and mobility was determined by loading analytical gels with a standard mixture of prestained polypeptides of known relative molecular mass (Biorad high molecular weight) as recited above and in the "Summary of the invention". The relative mobility of each polypeptide was calculated by manual measurement of the gels and plotted against $\log_{10}$ molecular mass. The gradient, calculated by regression analysis, was found to be linear, allowing molecular weights of unknowns to be determined by interpolation.

Laser scanning densitometry

The gels, stained and destained to reveal protein bands, were scanned by a laser scanning densitometer, whereby the intensity (optical density) of the bands is converted into a peak height and their size is represented by the area under the peak. Table 1 shows the relative molecular mass of the specific antigens and the relative amounts of protein represented by areas under peaks determined from the calibration plot. In FIG. 1 of the drawings, the SDS-PAGE bands were matched to the laser densitometric scan.

TABLE 1

Molecular weights and relative abundance of adipocyte antigens used for immunisation of sheep

| Antigen | Molecular wt (Daltons) | Abundance (% of total membrane protein) |
|---|---|---|
| 1a | 189019 ± 7345 | 3.05 |
| b | 178395 ± 8130 | |
| 2 | 127787 ± 3015 | 1.23 |
| 3 | 45488 ± 238 | 5.58 |
| 4 | 34729 ± 367 | 3.71 |
| 5 | 28014 ± 263 | 6.37 |
| 6 | 13608 ± 258 | 7.71 |
| A | 36949 ± 762 | 1.12 |
| B | 49553 ± 600 | 2.24 |
| C | 51244 ± 1123 | 4.07 |
| D | 121130 ± 2363 | 0.93 |
| E | 148368 ± 1761 | 1.21 |
| F | 162055 ± 1831 | 0.94 |
| H | 79900 | N.D. |

N.D. Not determined.

The standard errors for A, B, C and D were 2.0, 1.2, 2.2 and 2.0% respectively.

Section 4

Comparison of the pattern of reactive bands Seen with adipocyte plasma membranes with similarly treated membranes prepared from other porcine tissues and the use of such comparisons to identify adipocyte specific antigens of the adipocyte membrane Methods Preparation of porcine plasma membranes from tissues other than adipose Collection of tissues Tissues, other than adipose, were excised from freshly killed pigs. The samples were cut Into small pieces (2 g approx) and immersed In liquid nitrogen until completely frozen. The material was then stored at −70° C. until used.

Blood, for the preparation of red blood cell (rbc) membranes, was collected from the jugular vein of live pigs into heparinised tubes.

Preparation of tissue plasma membranes 10 g of each tissue was finely minced, then 20 ml of membrane extraction medium (MEM) consisting of 1.4 g $Na_2HPO_4$, 81.5 g sucrose, 0.83 g EDTA per liter and 20 µl of PMSF solution (0.2M stock solution) was added. This sample was then homogenised using a tissue homogeniser (3×10 second bursts), and the resulting homogenate centrifuged at 20,000 g for 20 min to remove dense particulate matter. The resulting supernatant was then centrifuged at 100,000 g for 1 hour In a Sorvall Combi ultracentrifuge. The resultant pellet was resuspended in 50 mM Tris/HCl.

Sucrose gradients were prepared in polypropylene tubes by overlaying solutions of 32, 36 and 40% sucrose. The pellets, suspended in Tris/HCl were then applied to the top of the gradient using a Pasteur pipette. The prepared gradient was then spun at 100,000 g for 1 hour.

Following centrifugation, a diffuse band of material was visible at the 0/32% interface. This was removed carefully by aspiration and washed in Tris and resuspended at an appropriate concentration.

Preparation of porcine red blood cell ghosts

Porcine red blood cell ghosts (i.e. de-haemoglobinised) were prepared using the method of Raval and Allan, Biochem. Biophys. Acta 856, 595–601 (1986). For this, 60 ml of fresh blood was collected into 10 ml heparinised tubes and spun at 2010 g. av. for 10 min. The plasma was then removed by aspiration and the remaining packed red cells washed three times by addition of 10 ml of isotonic Tris/HCl buffer (50 mM Tris, 150 mM NaCl, 4.2 mM HCl, adjusted with 1M NaOH to pH 7.4) followed by centrifugation at 2010 g. av. for 10 min. The cells were then lysed by the addition of 10 ml of hypotonic Tris/HCl buffer (50 mM Tris, 4.2 mM HCl, adjusted with 1M NaOH to pH 7.4). The cells suspended in this solution were left at room temperature for 10 min and then the mixture was centrifuged at 38720 g. av. for 10 min. The sedimented material was washed 3 times in the lysis buffer. Following this procedure, the membranes, when collected as a pellet, were pale pink to white in colour, with little residual haemoglobin present.

SDS-PAGE immunoblot analysis

Figure 2:
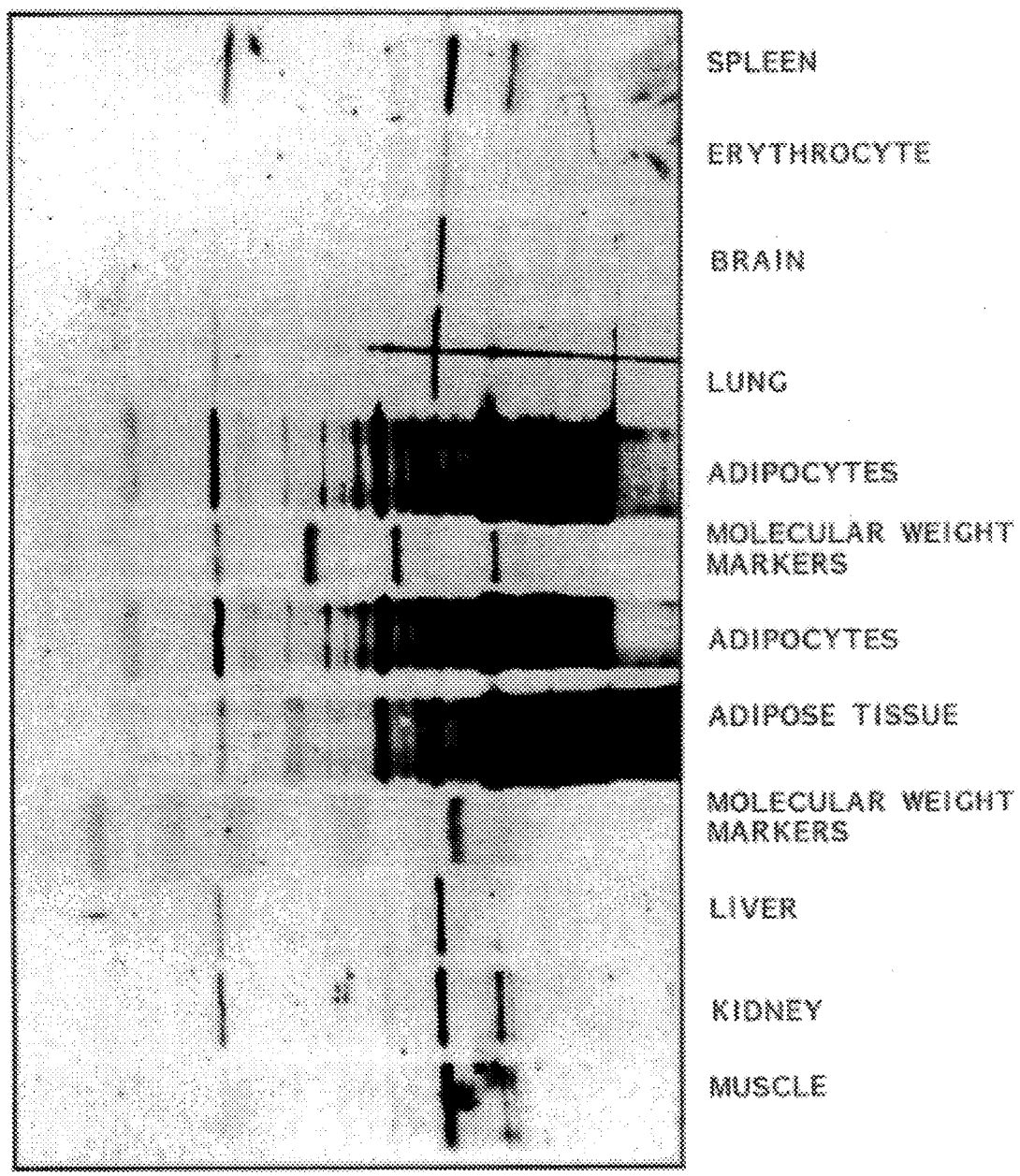
FIG. 2 is a photograph of an immunoblot showing the interaction of an antiserum to adipocyte plasma membranes with protein bands obtained from various porcine tissues including adipocyte plasma membranes.

FIG. 2 shows the pattern of bands reactive with sheep antibodies to porcine whole adipocyte plasma membranes in various porcine tissue plasma membranes indicating the high degree of reactivity with adipose tissue and the comparatively low reactivity with all other tissue types tested.

Laser densitometry of immunoblots of SDS-PAGE gels

First, (a) blots of SDS-PAGE gels that had been stained with Coomassie brilliant blue and (b) immunoblots of the same gels against sheep anti-porcine adipocyte plasma membranes, stained with 4-chloro-1-naphthol, were scanned using an enhanced laser densitometer (Ultroscan XL LKB). Data collected by the laser densitometer was analysed and stored using the Gelscan XL software package. This allowed comparisons to be made of the polypeptide composition of membranes resolved on SDS-PAGE and of immunoblots of membrane polypeptides (see below).

Sheep anti-porcine adipocyte plasma membrane was found to interact with plasma membranes prepared from other porcine tissues, although to a suprisingly low degree. Therefore, laser densitometric scanning, of the reactive bands in adipocyte plasma membranes and in membranes from other tissues, was used to identify adipocyte-specific antigens. That is, immunoblots from the gels of whole adipocyte plasma membranes were compared with immunoblots from the gels of membrane from other tissues, viz porcine liver, kidney, spleen, brain, muscle, lung and erythrocytes (red blood ghosts).

Identifying adipocyte-specific immunoreactive plasma proteins

The patterns/scans of reactive proteins from adipocyte plasma membranes were different from the patterns of the membrane proteins from other porcine tissues and which were themselves different from each other. However, closer comparison showed that some of the immuno-reactive proteins had similar mobilities although some appeared at specific different intensities of staining, related to the membrane type in question. To identify accurately those proteins that were definitely present only in adipocyte membranes on the blot, the Rf values of all the detected proteins in the different tissues were compared with the Rf values of the proteins from adipocytes. If any of the other tissues on the blot had proteins within 0.003 Rf units of any adipocyte membrane protein, then that protein was assumed to be not specific to adipocyte membranes.

This Rf comparison was performed for each blot separately, then the Rf values of amido black-stained molecular weight markers from each blot were used to plot calibration curves of molecular weight against Rf on logarithmic paper. These calibration curves were used to find the molecular weights of these initially identified adipocyte specific immunoreactive membrane components. The relative molecular masses of the specific adipocyte membrane proteins determined using separate blots were listed and compared. Those identified on four or more blots were considered to be reproducibly detectable adipocyte specific immunoreactive membrane components worthy of further investigation.

Results 12 adipocyte-specific antigens were thus found, having the relative molecular masses shown in Table 1 above. The number of determinations made was between 4 and 7 for each antigen. Biorad low molecular weight markers were used.

Section 5

Preparation of the above-identified antigens on a larger scale

14×12 cm gels (1.5 mm thick) were used to resolve larger samples of porcine adipocyte plasma membranes. The buffers and gel solutions used were as for the analytical gels. The gels were prepared and run in the same way, but in a larger electrophoresis unit. They were stained with Coomassie blue as described in Section 3. The procedure was found to be reproducible.

The bands from which polypeptides (A–F, H and 1–6) were to be eluted were excised from the gels and placed in the sample wells of an electrophoretic concentrator (Biorad mini-elutor). The proteins were electroeluted in a buffer of 25 mM Tris, 192 mM glycine, 0.1% SDS, pH 8.3 onto a 12,500 molecular weight cut off membrane. Elutions were run at a constant 100 V for 2–3 hours. Eluted samples were removed using a pasteur pipette.

Section 6

Removal of SDS and renaturation of polypeptides by dialysis against "QAE Sephadex" and non-ionic detergent Removal of the high salt concentration present in the protein samples after elution and exchange of SDS for a non-ionic non-denaturing detergent "Nonidet P40" was achieved by dialysis using a modification of the procedure of Hjertan, Biochem. Biophys. Acta 736, 130–136 (1983).

After elution as described above, the samples were placed in 6.3 mm dialysis tubing that had been boiled twice for 10 min in water containing 1 mM EDTA. They were then dialysed against 5 liters of 0.2 mM "Nonidet P40", containing 2 g of the anion exchanger "QAE Sephadex", to improve the efficiency of SDS removal. Dialysis was carried out for 25 hours at room temperature with the dialysate being changed after 12 hours.

Following dialysis, the samples were stored at −20° C.

Section 7

The use of the individual electroeluted membrane components as immunogens

Eluted proteins were mixed 1:2 with Freund's complete adjuvant for the 1st immunization and subsequently with Freund's incomplete adjuvant. Immunizations were given subcutaneously in 3 sites, 2 in the rump and 1 in the shoulder 4 weeks after the initial immunisation. Subsequent immunisations were carried out at 2 weekly intervals.

Section 8

The demonstration of antibody response using ELISA when each of the 12 individual antigens were administered as immunogens Serum samples collected from sheep injected with each antigen as in Section 7 were tested for their immunoreactivity with adipocyte plasma membrane (ELISA) or electrophoresed samples of individual antigens or whole adipocyte plasma membranes electroblotted onto Immobilon (immunoblotting).

ELISA

This was carried out according to the method of Flint et al. (1986). Briefly, porcine adipocyte plasma membranes (1 μg/well in PBS pH 7.4) were coated on to 96 well plates by incubating at 4° C. overnight and donkey anti-sheep IgG conjugated with horseradish peroxidase was used to detect antibody binding from the antisera raised in sheep against electroeluted antigen samples. Samples arising from sheep after the tertiary injection of immunogen (2nd bleed) were tested against ovine adipocyte plasma membranes. Antiserum collected from a sheep previously treated with porcine whole adipocyte plasma membranes was used as a positive control. The antisera raised against whole porcine adipocyte plasma membranes reacted strongly with the membranes immobilised on the plate, as did a number of the antisera against specific antigens. FIG. 3 (a) to (d) shows plots of four sets of ELISAs in which change in optical density per hour is plotted against the log.$_{10}$ of the dilution of the antiserum raised against each of the 12 specific antigens and against whole porcine adipocyte plasma membranes. It will be seen that antigen 6 did not react at all and F scarcely. These two were eliminated from further testing.

Section 9

Establishment of in vivo backfat test in pigs

The rapid testing of antisera for cytotoxicity to adipocytes in vivo

Figure 4A:
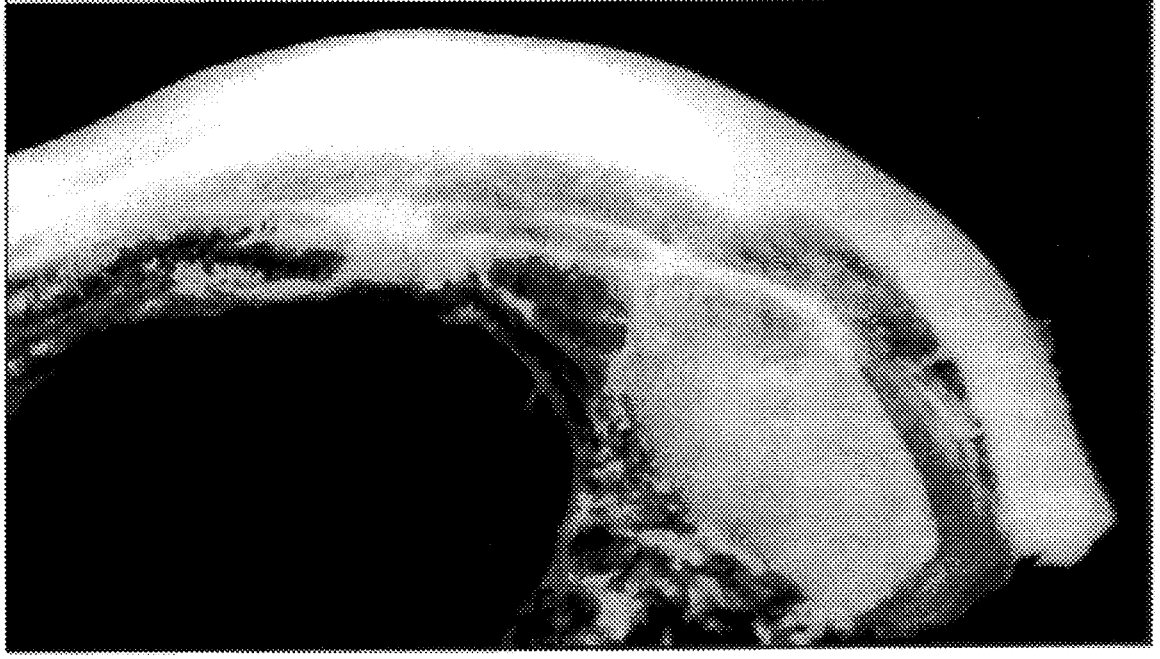
FIG. 4 (a) and (b) show sections through the backfat of pigs treated (a) with control antiserum and (b) with antibodies to whole adipocyte plasma membranes, illustrating the depletion of fat which occurs after adipocyte destruction.
Figure 4B:
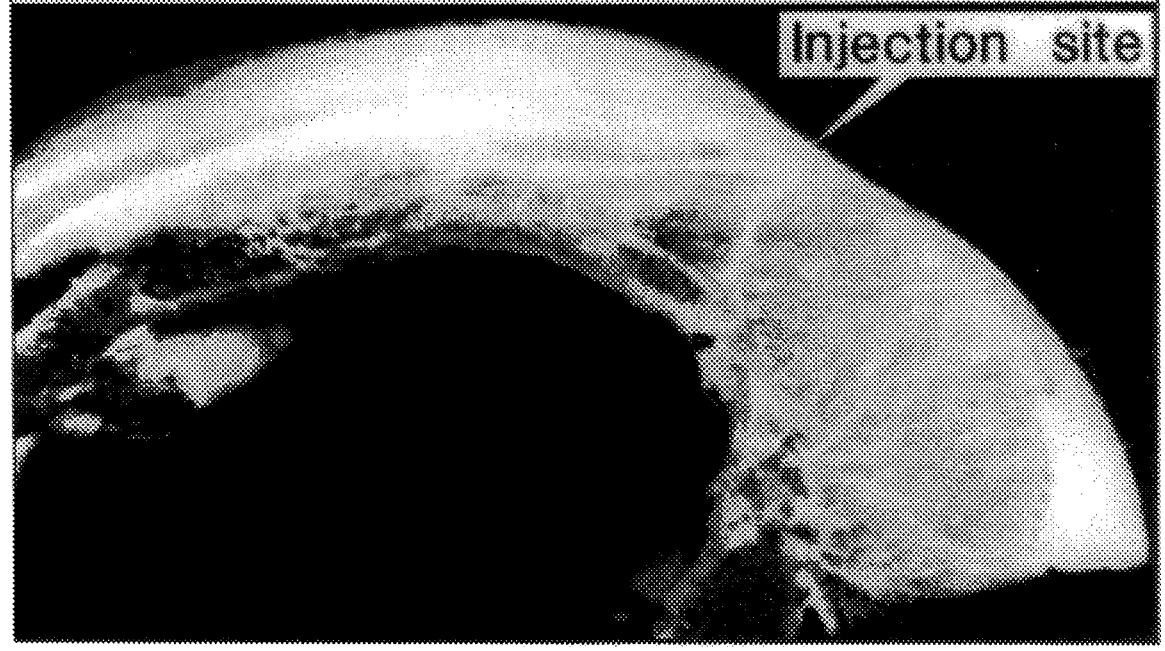
Figure 5A:
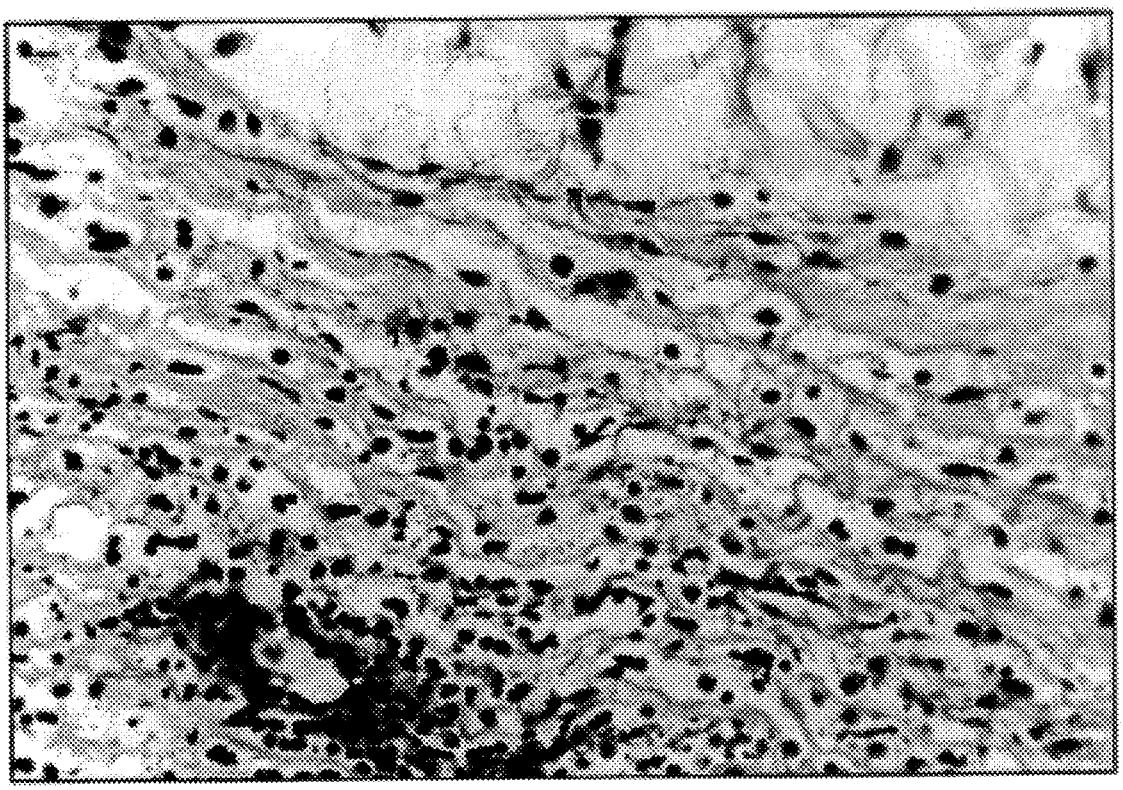
FIG. 5 (a), (b), (c) and (d) are photographs of typical histological sections of back fat treated with control serum (d) and antibodies of the invention (a, b, c) respectively.
Figure 5B:
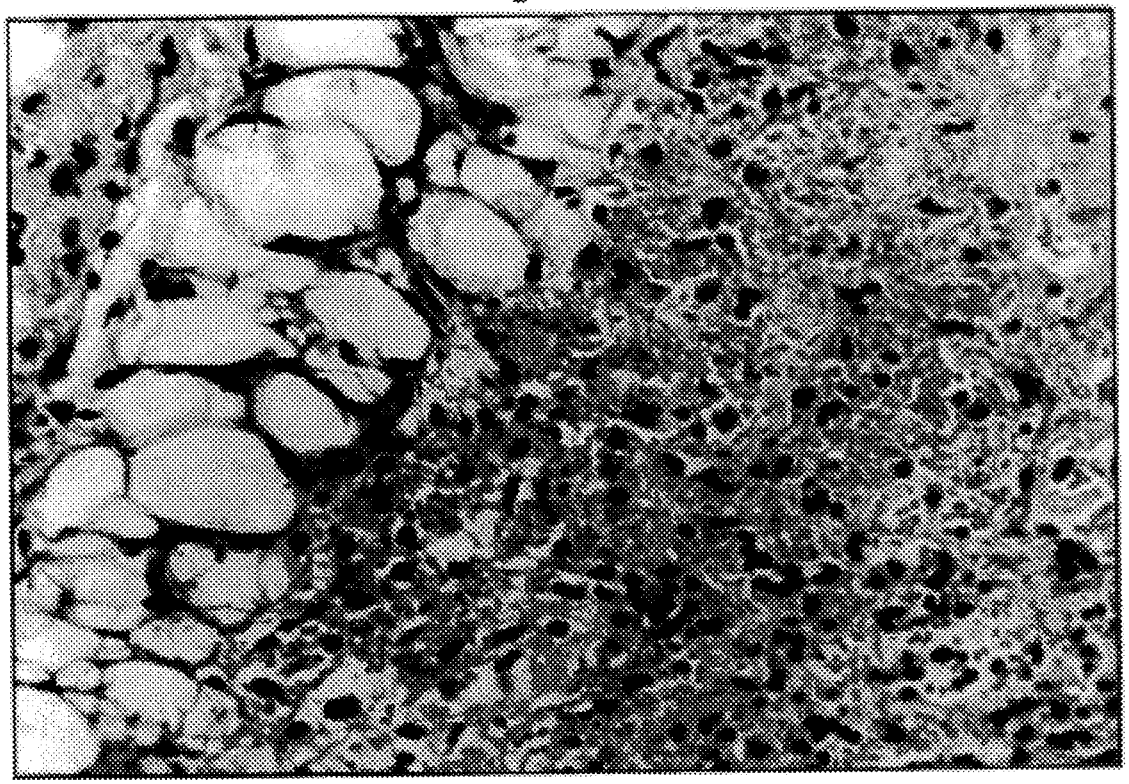
Figure 5C:
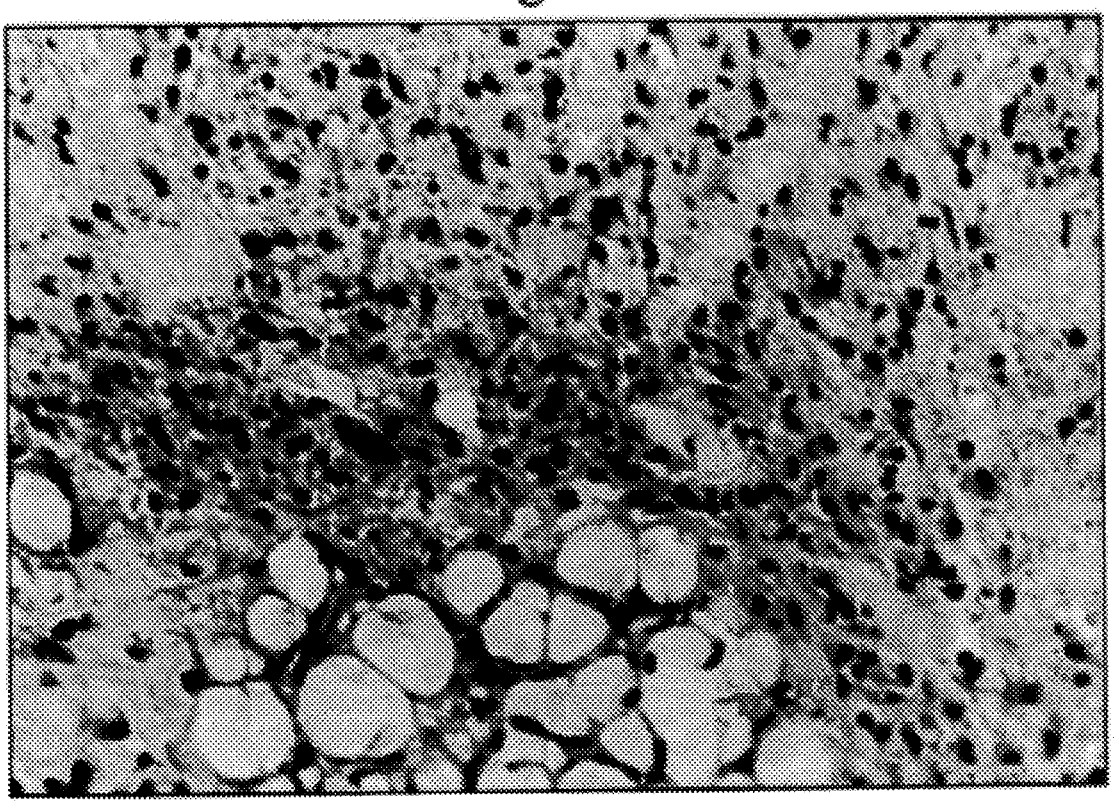
Figure 5D:
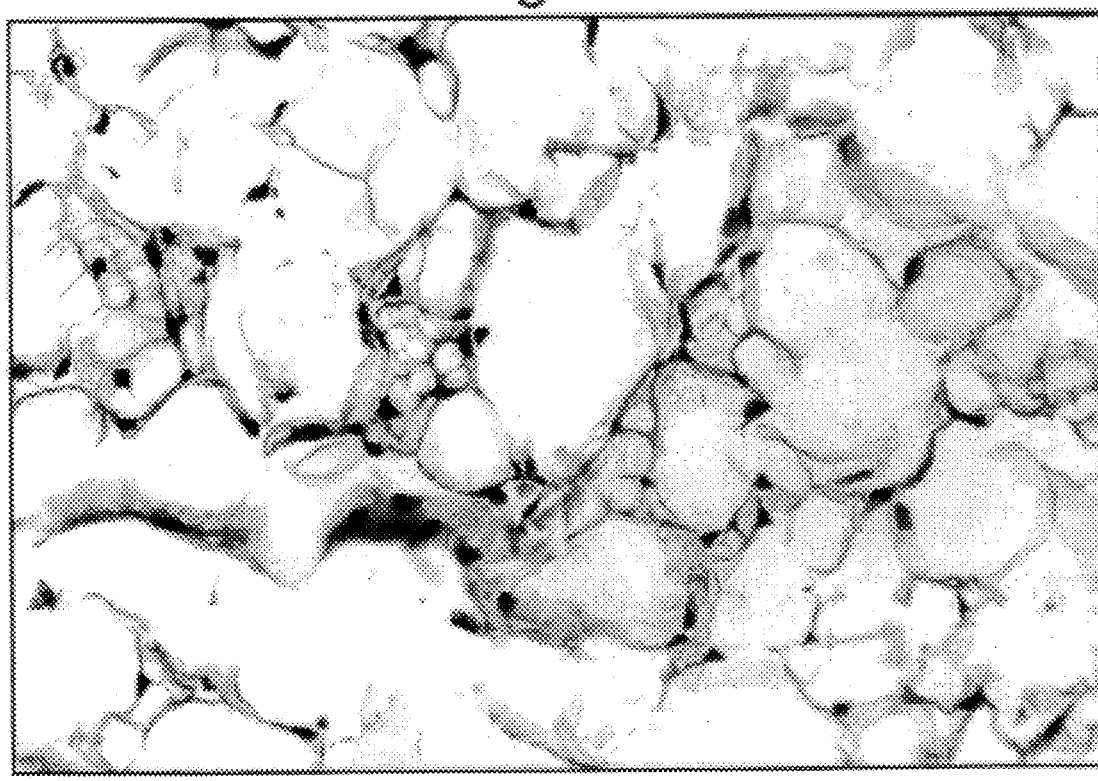

The 10 antisera raised against specific antigens and which gave a positive reaction in the ELISA were tested for their cytotoxicity towards Intact porcine adipocytes. The test involved the measurement of the very obvious lesion that develops around the site of injection of a cytotoxic antiserum. These lesions were first observed when pigs were passively immunised subcutaneously with an antiserum raised in sheep against whole porcine adipocyte plasma membranes. Briefly, after injection of the antiserum directly into a subcutaneous fat depot, areas of necrotic adipose tissue develop. One week after injection these sites will appear as areas of necrotic fat and inflamed tissue. Later the necrotic tissue degenerates, and after 8 weeks the site appears normal, but is devoid of fat, see FIG. 4 (b). No such lesion develops around the site of Injection of a control antiserum, FIG. 4 (a).

Pigs aged between 6 and 8 weeks were maintained on a standard pig starter diet. Injection sites were then marked with marker pen on the skin. These sites, four per side, were spaced 5 to 10 cm from the mid line and 10 cm apart. Areas known to be relatively devoid of subcutaneous fat were avoided.

The antisera from sheep immunised with individual porcine adipocyte plasma membrane antigens, positive control antisera from sheep immunised with whole pig adipocyte plasma membranes and negative control sera from sheep which had received no immunisation were prepared in an identical fashion, and stored at −20° C. Prior to injection, the antisera were thawed and loaded into individual syringes and warmed to room temperature. A mixture of equal proportions of the individual test antisera was also prepared (excluding the + and − control antisera) for comparison with the antisera to the whole membrane.

Each pig used received one injection of each of the positive and negative control antisera. In the remaining 6 sites, test antisera were allocated randomly. Each immunisation was of 1 ml, injected into the subcutaneous fat.

7 days after treatment, pigs were slaughtered by captive bolt, suspended by the hind legs and exsanguinated. After all blood flow had ceased, a rectangular strip of skin 40 cm wide and including all the injection sites and surrounding tissue was carefully peeled back by skinning down from the rump. This was left attached to the carcass at the neck (to avoid confusing the sites). Care was taken to remove the subcutaneous adipose tissue with the skin.

The entire area of skin was examined for any areas of necrosis and damage. Large lesions were obvious, and small lesions were detectable as an area of yellowing tissue. The entire area of skin was examined, and lesions found related to the injection marks on the skin. After measurement with callipers and photography, samples of lesion tissue from each site, and control samples from sites distant from any injection site were removed and stored in formalin buffered saline for histology.

The sizes of the lesions seen in at least 3 independent studies are shown in Table 2. Photographs are provided as FIGS. 5 (a) to (d). FIG. 5 (d) shows the fat cells in a section from a control animal, where the fat cells have a large triglyceride droplet stored in the centre of the cell (which appears white in the photographs). Contrast FIG. 5 (a), (b) and (c) which are typical of the animals treated according to the invention with antisera to antigens A, B and C, respectively, in which the dark areas represent lymphocyte cells infiltrating the adipose tissue.

TABLE 2

Effects of antisera raised against individual specific antigens on adipose tissue in vivo

| Antiserum to: | Dose (ml) | Area of destruction (mm) |
|---|---|---|
| Whole membrane | 2 | 35 |
|  | 0.4 | 6.5 |
|  | 0.2 | 3.5 |
|  | 0.02 | 0 |
| Antigen |  |  |
| A | 2 | 2 |
| B | 2 | 3 |
| C | 2 | 3.5 |
| D | 2 | 2 |
| E | 2 | 0 |
| H | 2 | 0 |

TABLE 2-continued

Effects of antisera raised against individual specific antigens on adipose tissue in vivo

| Antiserum to: | Dose (ml) | Area of destruction (mm) |
|---|---|---|
| 1 | 2 | 0 |
| 2 | 2 | 0 |
| 3 | 0 | |
| 4 | 2 | 0 |
| 5 | 2 | 0 |
| Non-immune serum control | 2 | 0 |

Pigs received a single subcutaneous injection of antiserum at various sites on the back, After 7 days the size of the site of adipocyte destruction was determined.

Results are the mean values obtained from at least 3 separate experiments.

A problem in evaluating the results of Table 2 concerns the effective amounts of antibody raised. The electroelution procedure employed in preparation of the specific antigens has probably resulted in some degradation of proteins. Therefore, the antisera might have been raised against components of the higher relative molecular mass antigens, rather than full length proteins. This makes it particularly difficult to compare amounts of effective epitope even with the benefit of the ELISA data.

Notwithstanding these limitations, it was surprising to note that some antisera (anti-A and -B) which reacted strongly with adipocyte plasma membranes In ELISA also elicited adipocyte lysis in vivo whilst all the others except C and D, several of which reacted at least as well In ELISA, failed to produce adipocyte destruction (compare FIG. 3 and Table 2).

We claim:

1. An isolated antigen present in the plasma membrane of mature porcine white adipocytes, which is not detectable in porcine liver, kidney, spleen, brain, cardiac muscle, skeletal muscle or lung or in porcine erythrocytes, which reacts with antisera raised against said adipocytes, said antigen being selected from the group consisting of a 37, 50, 51, and 121 KiloDaltons relative molecular mass antigen as determined by SDS-PAGE using markers of relative molecular mass 29, 45, 66, 97, 116, and 205 KiloDaltons.

2. Isolated antibodies that are specific to one of said antigens claimed in claim 1.

3. Isolated antibodies according to claim 2 which are monoclonal.

4. A method of reducing fat in pigs by active immunization which comprises administering to the pig an amount of an immunogen which comprises an antigen claimed in claim 1, said immunogen having been rendered effective to elicit an immune response to adipocytes.

5. A method according to claim 4 wherein the immunogen is rendered effective to elicit an immune response by conjugation to a carrier protein.

6. A method of reducing fat in pigs by passive immunisation which comprises administering antibodies claimed in claim 2 or 3 to the pig in an amount effective to immunise the pig against fat deposition.

* * * * *